(12) United States Patent
Moriya

(10) Patent No.: US 7,852,476 B2
(45) Date of Patent: Dec. 14, 2010

(54) PARTICLE MONITOR SYSTEM AND SUBSTRATE PROCESSING APPARATUS

(75) Inventor: Tsuyoshi Moriya, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 386 days.

(21) Appl. No.: 11/969,501

(22) Filed: Jan. 4, 2008

(65) Prior Publication Data
US 2008/0170226 A1    Jul. 17, 2008

Related U.S. Application Data

(66) Substitute for application No. 60/911,376, filed on Apr. 12, 2007.

(30) Foreign Application Priority Data

Jan. 16, 2007    (JP)    ............... 2007-007367

(51) Int. Cl.
*G01N 21/00* (2006.01)
(52) U.S. Cl. ...................... 356/338; 250/574
(58) Field of Classification Search ......... 356/335–343; 73/28.01, 28.08, 31.05; 250/573, 574
See application file for complete search history.

(56) References Cited

U.S. PATENT DOCUMENTS

| | | | | |
|---|---|---|---|---|
| 5,271,264 A | * | 12/1993 | Chanayem | ................. 73/28.01 |
| 5,534,706 A | * | 7/1996 | Borden et al. | ................. 250/574 |
| 5,837,094 A | * | 11/1998 | Tsukazaki et al. | ....... 156/345.25 |
| 6,947,134 B2 | * | 9/2005 | Chang et al. | ................. 356/318 |
| 2005/0145333 A1 | * | 7/2005 | Kannan et al. | ......... 156/345.24 |
| 2008/0240905 A1 | * | 10/2008 | Sugawara et al. | ......... 415/121.2 |
| 2008/0264338 A1 | * | 10/2008 | Otsuki et al. | ................. 118/712 |

FOREIGN PATENT DOCUMENTS

JP        9-203704        8/1997

* cited by examiner

*Primary Examiner*—Hoa Q Pham
(74) *Attorney, Agent, or Firm*—Oblon, Spivak, McClelland, Maier & Neustadt, L.L.P.

(57) ABSTRACT

A particle monitor system capable of accurately detecting the number of or the size of particles flowing through an exhaust pipe. In a bypass line through which a chamber is communicated with a dry pump, there is disposed the particle monitor system that includes a laser oscillator for irradiating laser light, a photo multiplier tube having a focal point thereof located at a location where the center axis of the bypass line crosses the laser light, and a particle converging member formed by a circular disk-like member and formed with a through hole facing the focal point FP. A gap is defined between the bypass line and an outer periphery of the particle converging member.

7 Claims, 10 Drawing Sheets

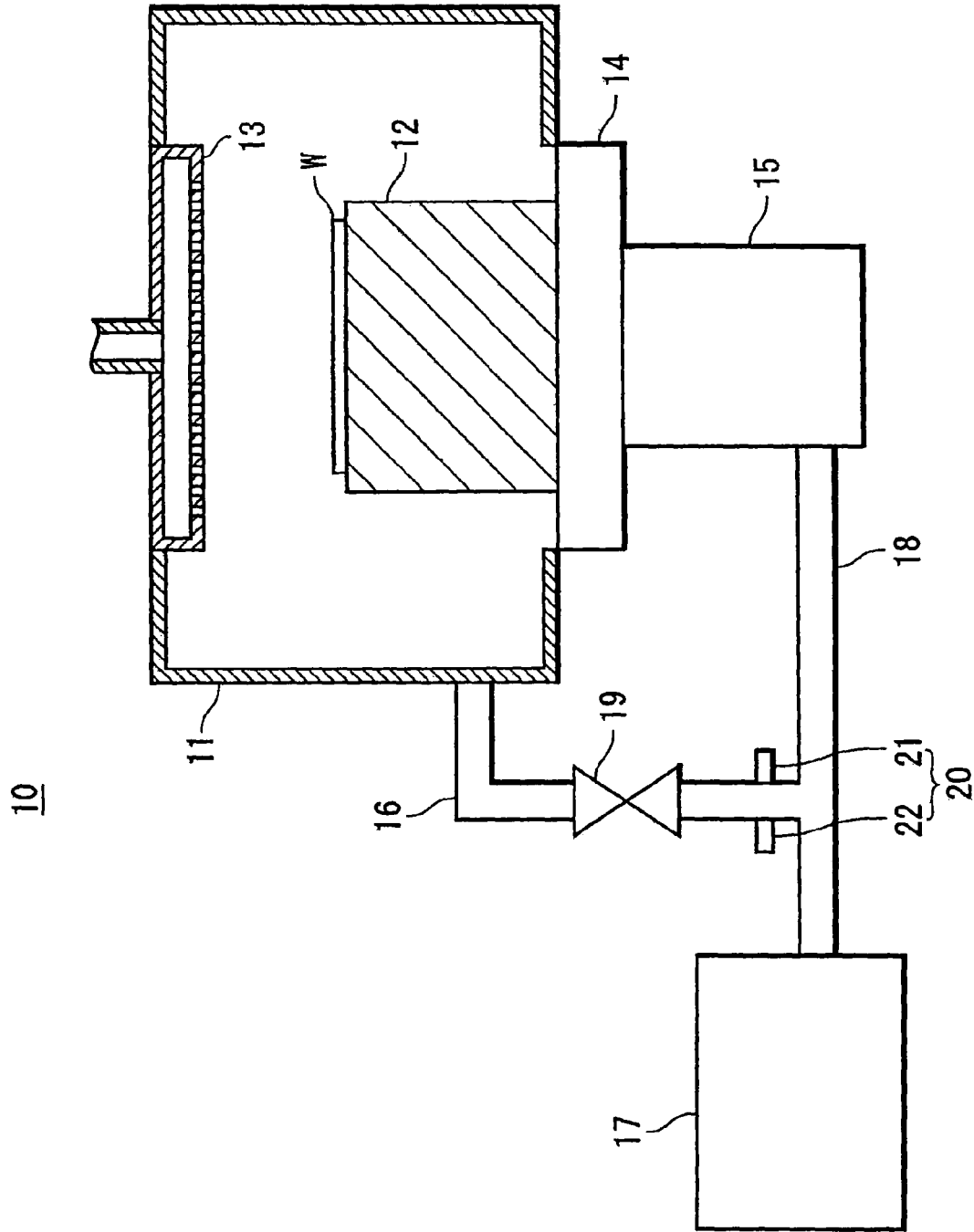

PARTICLE MONITOR SYSTEM AND SUBSTRATE PROCESSING APPARATUS

BACKGROUND OF THE INVENTION

1. Field of the Invention

The present invention relates to a particle monitor system and a substrate processing apparatus, and more particularly, to a particle monitor system for detecting the number of particles flowing through an exhaust pipe of a substrate processing apparatus, and a substrate processing apparatus including the same.

2. Description of the Related Art

A substrate processing apparatus is known that includes a chamber for housing a wafer as substrate and an exhaust pipe for discharging particles and gases from the chamber. In this apparatus, a plasma is generated in the chamber and used to perform desired plasma processing on a wafer. While the plasma processing is repeatedly performed, particles resulting from reaction products and/or deposits are generated in the chamber. With the increasing number of particles in the chamber, particles adhered to wafers increases, resulting in a low yield of semiconductor devices from wafers. It is therefore necessary to regularly detect the number of particles in the chamber and clean the interior of the chamber when the number of particles exceeds a predetermined threshold value.

As a method for detecting the number of particles in the chamber, it is known to detect the number of particles in a sub-chamber, which is provided adjacent to the chamber (see Japanese Laid-open Patent Publication No. 9-203704), or detect the number of particles flowing through an exhaust pipe, and estimate the number of particles in the chamber based on a result of the detection.

An ISPM (In Situ Particle Monitor) is usually used for the detection of the number of particles in the sub-chamber or the exhaust pipe. For example, the ISPM includes a laser oscillator for irradiating laser light toward inside the exhaust pipe, a photo multiplier tube (PMT) for observing light scattered by particles passing through the laser light, and a PC for detecting the number of particles in the chamber based on the intensity of observed scattered light and so on.

In the ISPM, since the laser light irradiated to the inside of the exhaust pipe is narrow in width, particles passing through the laser light are only part of the particles flowing inside the exhaust pipe, thus making it impossible to accurately detect the number of particles flowing through the exhaust pipe. To obviate this, methods have been developed, in which laser light is broadened into a belt shape to irradiate the entire section of the exhaust pipe or the inside of the exhaust pipe is scanned by laser light, so that most of particles flowing through the exhaust pipe are made to pass through the laser light.

In the method of broadening laser light into a belt shape, however, scattered light is low in intensity, which makes it difficult to detect minute particles. On the other hand, in the method of scanning the inside of the exhaust pipe with laser light, particles flowing at high speeds can sometimes pass through that region of the exhaust pipe which is scanned with the laser light, without crossing the laser light. Thus, some of the particles flowing at high speeds cannot be detected. In addition, since there are produced stray light and noise at the time of scanning, it is sometimes determined that particles had passed through the laser light even though particles do not actually pass therethrough. In other words, it is still difficult to accurately detect the number or size of particles flowing through the exhaust pipe.

SUMMARY OF THE INVENTION

The present invention provides a particle monitor system capable of accurately detecting the number or size of particles passing through an exhaust pipe of a substrate processing apparatus, and provides a substrate processing apparatus including such a particle monitor system.

According to a first aspect of this invention, there is provided a particle monitor system for detecting particles in a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising a laser oscillator adapted to irradiate laser light toward inside the exhaust pipe, a light receiving device having a focal point thereof adapted to be located on the laser light, the light receiving device being adapted to receive scattered light or attenuated light of the laser light scattered or attenuated by particles flowing through the exhaust pipe, and a particle converging unit adapted to converge at least part of the particles toward the focal point of the light receiving device, wherein the particle converging unit includes a gas passage through which gas passes from upstream of the exhaust pipe to downstream thereof.

With this particle monitor system, particles in the exhaust pipe are converged toward that focal point of the light receiving device which is located on the laser light, whereas gas passes through the gas passage of the particle converging unit. As a result, most of the particles flowing through the exhaust pipe can be made to pass through the laser light, without the need of broadening the laser light into a belt-shape or without the inside of the exhaust pipe being scanned by the laser light, thus making it possible to accurately detect the number or size of particles flowing through the exhaust pipe, and prevent the conductance of the flow of gas from being lowered whereby a reduction in the efficiency of discharging the gas from inside the housing chamber can be prevented.

In this invention, the gas passage of the particle conversing unit can be adapted to introduce the gas toward a location other than the focal point of the light receiving device.

In that case, since the gas is guided to flow toward a location other than the focal point of the light receiving device, the flow of the gas does not disturb the flow of particles at or near the focal point, making it possible to more accurately detect the number or size of particles flowing through the exhaust pipe.

A pressure in the exhaust pipe upon detection of particles can be set to a value in a range from 100 Pa to 10 kPa.

In that case, upon detection of particles, the pressure inside the exhaust pipe is set to a value falling within a range from 100 Pa to 10 kPa. When the pressure falls within such a range, an inertia force acting on particles becomes relatively large, and therefore, the flow of particles is hardly disturbed by gas flow, making it possible to efficiently converge the particles toward that focal point of the light receiving device which is located on the laser light.

The particle converging unit can be comprised of at least one plate-like member disposed to obstruct the exhaust pipe, the plate-like member can be formed with a hole facing the focal point of the light receiving device, and the gas passage of the particle converging unit can be formed at a location other than a location where the hole of the plate-like member is formed.

In that case, the plate-like member of the particle converging unit has a hole facing the focal point of the light receiving device, and the gas passage is formed at a location other than a location where the hole is formed. By causing particles to pass through the hole, therefore, the particles can efficiently be converged toward the focal point of the light receiving device located on the laser light, and a gas flow disturbing the flow of particles can reliably be prevented from being generated at or near the focal point.

The particle converging unit can be comprised of a plurality of the plate-like members, and holes formed in those of the plate-like members which are disposed closer to the focal point of the light receiving device can be made smaller in diameter.

In that case, the holes formed in plate-like members of the particle converging unit disposed closer to the focal point of the light receiving device are smaller in diameter. Therefore, by causing particles to pass through these holes, the flow of particles can be straightened toward the focal point, whereby it is ensured that the particles are converged toward the focal point located on the laser light.

The particle converging unit can be comprised of at least one funnel-shaped member having a bottom portion thereof formed with an opening facing the focal point of the light receiving device, and the gas passage can be formed at a location other than a location where the opening of the funnel-shaped member is formed.

In that case, the funnel-shaped member of the particle converging unit has its bottom portion formed with the opening that faces the focal point of the light receiving device, and the gas passage of the particle converging unit is formed at a location other than a location where the opening of the funnel-shaped member is formed. By causing particles to pass through the opening of the particle converging unit, therefore, the particles can efficiently be converged toward focal point located on the laser light, and a gas flow disturbing the flow of particles can reliably be prevented from being generated at or near the focal point.

The particle converging unit can be comprised of a plurality of the funnel-shaped members, and those of the funnel-shaped members which are disposed closer to the focal point can be made smaller in size of openings thereof.

In that case, funnel-shaped members of the particle-converging unit disposed closer to the focal point of the light receiving device have their openings which are made smaller in size. By causing particles to pass through these openings of the particle converging unit, therefore, the flow of the particles can be straightened toward the focal point of the light receiving device, thereby ensuring that the particles can be converged toward the focal point located on the laser light.

The particle converging unit can be comprised of a plurality of tubular members each having a shape tapered toward downstream of the exhaust pipe and each having at its tip end an opening thereof facing the focal point of the light receiving device, each of the openings of the particle converging unit also serving as the gas passage of the particle converging unit.

In that case, each of the tubular members of the particle converging unit has a shape tapered toward downstream of the exhaust pipe and is formed at its tip end with an opening that faces the focal point and also serves as a gas passage. By causing particles to pass through the openings of the particle converging unit, therefore, it is ensured that the particles can efficiently be converged toward the focal point on the laser light, and the gas passage of the particle converging unit can be constituted by the openings of the particle converging unit, making it possible to positively prevent a reduction in conductance of gas flow.

According to a second aspect of this invention, there is provided a particle monitor system for detecting particles in a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising a laser oscillator adapted to irradiate laser light toward inside the exhaust pipe, a light receiving device having a focal point thereof adapted to be located at a location at which a center axis of the exhaust pipe crosses the laser light, the light receiving device being adapted to receive scattered light or attenuated light of the laser light scattered or attenuated by particles flowing through the exhaust pipe, and a vortex flow generator adapted to generate a vortex flow of gas that rotates around the center axis of the exhaust pipe.

With this particle monitor system, the light receiving device has its focal point at a location where the center axis of the exhaust pipe crosses the laser light, and a vortex gas flow rotating around the center axis of the exhaust pipe is generated. Since the vortex gas flow applies a centripetal force onto particles flowing through the exhaust pipe, the particles are converged toward the focal point of the light receiving device, which is located on the center axis of the exhaust pipe. Thus, without the need of broadening the laser light into a belt-shape or the inside of the exhaust pipe being scanned by the laser light, it is possible to cause most of the particles flowing through the exhaust pipe to pass through the laser light, thereby making it possible to accurately detect the number or the size of the particles flowing through the exhaust pipe.

A pressure in the exhaust pipe upon detection of particles can be set to a value in a range from 1000 Pa to 100 kPa.

In that case, upon detection of particles, a pressure in the exhaust pipe is set to a value falling within a range from 1000 Pa to 100 kPa. When the pressure falls within such a range, a viscous force of the gas produced by the gas flow increases, and therefore, a centripetal force is applied to the particles, whereby it is ensured that the particles are converged toward the focal point of the light receiving device, which is located on the center axis of the exhaust pipe.

According to a third aspect of this invention, there is provided a particle monitor system for detecting particles in a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising a laser oscillator adapted to irradiate laser light toward inside the exhaust pipe, a light receiving device having a focal point thereof adapted to be located on the laser light, the light receiving device being adapted to receive scattered light or attenuated light of the laser light scattered or attenuated by particles flowing through the exhaust pipe, a cooling unit adapted to cool atmosphere around the focal point, and a heating unit adapted to heat atmosphere other than atmosphere around the focal point.

With this particle monitor system, atmosphere around the focal point of the light receiving device is cooled, whereas atmosphere other than around the focal point is heated. Since particles are moved away from high temperature atmosphere by a heat migrating force, the particles are converged in the exhaust pipe toward the focal point of the light receiving device, which is located on the laser light. Thus, without the need of broadening the laser light into a belt-shape or without the inside of the exhaust pipe being scanned by the laser light, it is possible to cause most of the particles flowing through the exhaust pipe to pass through the laser light, making it possible to accurately detect the number or the size of the particles flowing through the exhaust pipe. In addition, since the provision of a plate-like member for closing the exhaust pipe is unnecessary, the conductance of gas flow can be prevented from being decreased.

According to a fourth aspect of this invention, there is provided a particle monitor system for detecting particles in a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising a laser oscillator adapted to irradiate laser light toward inside the exhaust pipe, a light receiving device having a focal point thereof adapted to be located on the laser light, the light receiving device being adapted to receive scattered light or attenuated light of the laser light scattered or attenuated by particles flowing through the exhaust pipe, a charging device disposed upstream of the focal point and adapted to cause the particles to be charged, and an electrode disposed around the focal point.

With this particle monitor system, there are provided a charging device disposed upstream of the focal point for causing particles to be charged and an electrode disposed around the focal point. Charged particles are attracted toward the focal point of the light receiving device by an electrostatic force generated by the electrode applied with a voltage, and therefore, the particles are converged in the exhaust pipe toward the focal point located on the laser light. Thus, without the need of broadening the laser light into a belt-shape or without the inside of the exhaust pipe being scanned by the laser light, it is possible to cause most of the particles flowing through the exhaust pipe to pass through the laser light, making it possible to accurately detect the number or the size of the particles flowing through the exhaust pipe. In addition, since the provision of a plate-like member for closing the exhaust pipe is unnecessary, the conductance of gas flow can be prevented from being decreased.

According to a fifth aspect of this invention, there is provided a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising a laser oscillator adapted to irradiate laser light toward inside the exhaust pipe, a light receiving device having a focal point thereof adapted to be located on the laser light, the light receiving device being adapted to receive scattered light or attenuated light of the laser light scattered or attenuated by particles flowing through the exhaust pipe, and a particle converging unit adapted to converge at least part of the particles toward the focal point of the light receiving device, wherein the particle converging unit includes a gas passage through which gas passes from upstream of the exhaust pipe to downstream thereof.

According to a sixth aspect of this invention, there is provided a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising a laser oscillator adapted to irradiate laser light toward inside the exhaust pipe, a light receiving device having a focal point thereof adapted to be located at a location at which a center axis of the exhaust pipe crosses the laser light, the light receiving device being adapted to receive scattered light or attenuated light of the laser light scattered or attenuated by particles flowing through the exhaust pipe, and a vortex flow generator adapted to generate a vortex flow of gas that rotates around the center axis of the exhaust pipe.

According to a seventh aspect of this invention, there is provided a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising a laser oscillator adapted to irradiate laser light toward inside the exhaust pipe, a light receiving device having a focal point thereof adapted to be located on the laser light, the light receiving device being adapted to receive scattered light or attenuated light of the laser light scattered or attenuated by particles flowing through the exhaust pipe, a cooling unit adapted to cool atmosphere around the focal point, and a heating unit adapted to heat atmosphere other than atmosphere around the focal point.

According to an eighth aspect of this invention, there is provided a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising a laser oscillator adapted to irradiate laser light toward inside the exhaust pipe, a light receiving device having a focal point thereof adapted to be located on the laser light, the light receiving device being adapted to receive scattered light or attenuated light of the laser light scattered or attenuated by particles flowing through the exhaust pipe, a charging device disposed upstream of the focal point and adapted to cause the particles to be charged, and an electrode disposed around the focal point.

With the substrate processing apparatuses according to the fifth to eighth aspects of this invention, advantages similar to those attained by the particle monitor systems according to the first to fourth aspects can be attained.

Further features of the present invention will become apparent from the following description of exemplary embodiments with reference to the attached drawings.

BRIEF DESCRIPTION OF THE DRAWINGS

FIG. 1 is a section view schematically showing the construction of a substrate processing apparatus according to a first embodiment of this invention;

DETAILED DESCRIPTION OF THE PREFERRED EMBODIMENTS

Figure 2A:
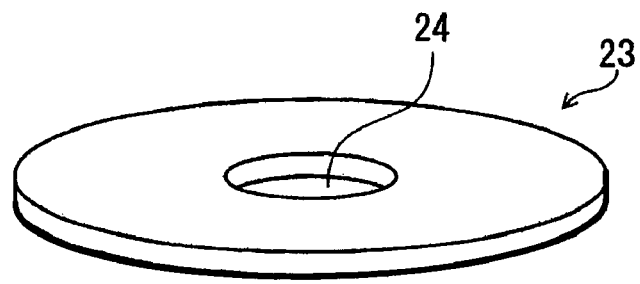
FIG. 2A is a perspective view schematically showing the construction of a particle converging member of the first embodiment.

The present invention will now be described in detail below with reference to the drawings showing preferred embodiments thereof.

First, an explanation will be given of a substrate processing apparatus according to a first embodiment of this invention.

FIG. 1 schematically shows the construction of the substrate processing apparatus of this embodiment in section view.

As shown in FIG. 1, the substrate processing apparatus 10 includes a chamber (housing chamber) 11 adapted to house a semiconductor wafer (hereinafter referred to as the wafer) having a diameter of, e.g., 300 mm, a cylindrical susceptor 12 disposed in a lower part of the chamber 11, and a shower head 13 disposed in an upper part of the chamber 11 to face the susceptor 12.

A wafer W received in the chamber 11 is placed on the susceptor 12, and processing gas or the like is supplied into the chamber 11 from the shower head 13. In the chamber 11, plasma is generated from the supplied processing gas, and the wafer W is subjected to plasma processing such as etching using the plasma. In this apparatus 10, particles resulting from reaction products and/or deposits are generated in the chamber 11 while the plasma processing is repeatedly carried out.

The chamber 11 is communicated, on one hand, with a TMP (Turbo Molecular Pump) 15 via an APC (Adaptive Pressure Control) valve 14 and is communicated, on the other hand, with a DP (Dry Pump) 17 (exhausting apparatus) via a cylindrical bypass line 16 (exhaust pipe). The TMP 15 is communicated via a main line 18 to the bypass line 16 in the middle of which a valve 19 is disposed. The pressure in the chamber 11 is controlled by the APC valve 14, and the bypass line 16 is opened and closed by the valve 19.

Gases and particles in the chamber 11 are discharged by the DP 17 from the chamber 11 via the bypass line 16. The pressure in the chamber 11 is reduced by the DP 17 from atmospheric pressure to a low vacuum state. The TMP 15 cooperates with the DP 17 to reduce the pressure in the chamber 11 from a low vacuum state to a high vacuum state (for example, to a pressure equal to or less than 133 Pa (1 Torr)), which is lower than the pressure in the low vacuum state.

An ISPM (In Situ Particle Monitor) 20 is disposed in the bypass line 16 between the valve 19 and the DP 17. The ISPM 20 includes a laser oscillator 21 for irradiating laser light toward the center axis of the bypass line 16, and a photo multiplier tube 22 (light receiving device) having a focal point FP thereof located at a location where the center axis of the bypass line 16 crosses the laser light (see FIG. 2B). The photo multiplier tube 22 receives scattered light generated in the bypass line 16 when particles pass through the irradiated laser light, or receives laser light (attenuated light) attenuated by particles. The scattered or attenuated light is converted into an electrical signal, which is then transmitted to a PC (not shown). Based on the transmitted electrical signal, the PC detects the number or size of particles flowing through the bypass line 16.

Upon estimation of the number or size of particles in the chamber 11 using the ISPM 20, the APC 14 is closed and the valve 19 is opened, the inside of the chamber 11 is depressurized by the DP 17, and a large amount of $N_2$ gas or dry air is introduced from the shower head 13 into the chamber 11, whereby the pressure in the chamber 11 is maintained at 133 Pa (1 Torr). At a pressure equal to or higher than 133 Pa, a viscous force of $N_2$ gas or the like acts on particles in the chamber 11, and the $N_2$ gas or the like in which particles are mixed is sucked into the bypass line 16. As a result, the particles in the chamber 11 flow through the bypass line 16. At that time, the particles flow through the bypass line 16, while repeatedly colliding with and reflected by an inner wall of the bypass line 16. The ISPM 20 detects the number or size of particles flowing through the bypass line 16.

Figure 2B:
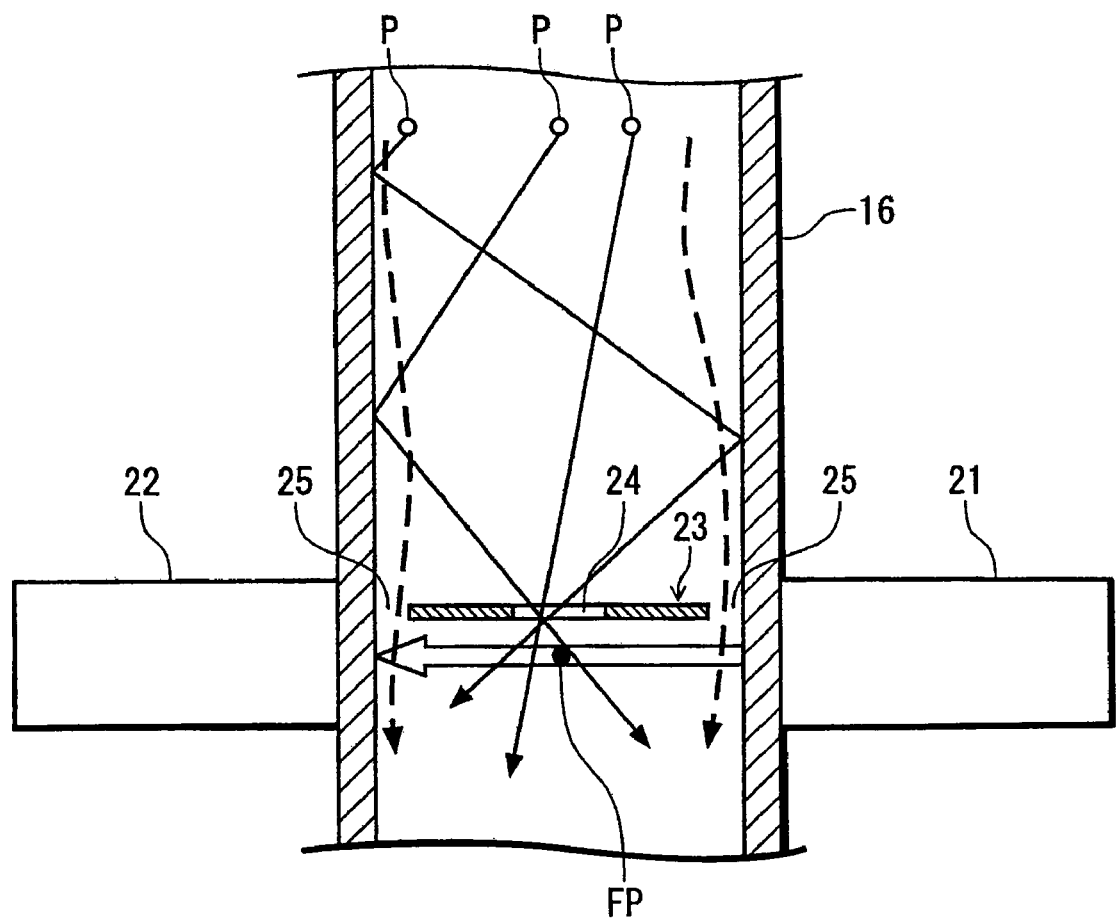
FIG. 2B is a section view showing the particle converging member in a state arranged in a bypass line.

In this embodiment, to converge the particles flowing through the bypass line 16, a particle converging member 23 (particle converging unit) is disposed in the bypass line 16 at a location upstream of the focal point FP of the photo multiplier tube 22, as shown in FIGS. 2A and 2B.

FIG. 2A schematically shows in perspective view the construction of the particle converging member 23, and FIG. 2B shows in section view the particle converging member 23 in a state arranged in the bypass line 16. In FIG. 2B, laser light is indicated by white blank arrow.

As shown in FIG. 2A, the particle converging member 23 is comprised of a circular disk-like member and formed at its center part with a through hole 24. The particle converging member 23 has its outer diameter smaller than an inner diameter of the bypass line 16 by a predetermined value, for instance, by 5 mm.

The particle converging member 23 is disposed in the bypass line 16 such that its center coincides with the center axis of the bypass line 16, and is disposed upstream of the focal point FP of the photo multiplier tube 22 by a predetermined value, for instance, 10 mm. In other words, the particle converging member 23 is disposed to obstruct the bypass line 16, with its through hole 24 facing the focal point FP and with a gap 25 (gas passage) formed between an inner periphery of the bypass line 16 and an outer periphery of the particle converging member 23.

Since the particle converging member 23 is disposed to obstruct the bypass line 16, most of particles P flowing through the bypass line 16 pass through the through hole 24 of the particle converging member 23. Since the through hole 24 of the particle converging member 23 faces the focal point FP, the particles P passing through the through hole 24 naturally pass through the vicinity of the focal point FP. In other words, the particle converging member 23 converges most of the particles toward the focal point FP.

N₂ gas or the like flowing through the bypass line 16 passes through the gap 25 from upstream side to downstream side, as shown by dotted line in FIG. 2B. Since the gap 25 is formed at the outer periphery of the particle converging member 23, N₂ gas or the like is introduced via the gap 25 toward a location other than the focal point FP in the bypass line 16.

Since the bypass line 16 is disposed closer to the DP 17 than to the chamber 11, the pressure in the bypass line 16 is made lower than the pressure in the chamber 11. Specifically, the pressure in the bypass line 16 in the vicinity of ISPM 20 is set to a value falling in a range from 100 Pa (750 mTorr) to 10 kPa (75 Torr). The lower the pressure, the smaller the viscous force of N2 gas or the like will be. Thus, the inertia force acting on the particles P becomes relatively large. When the pressure is at 100 Pa, the inertia force acting on the particles P becomes larger than the viscous force of N₂ gas or the like. Therefore, particles P are not caught into the flow of N₂ gas or the like in the vicinity of the ISPM 20 in the bypass line 16.

In this embodiment, the laser oscillator 21 cooperates with the photo multiplier tube 22 and the particle converging member 23 to constitute a particle monitor system.

With the substrate processing apparatus 10 of this embodiment having the particle monitor system, most of the particles P in the bypass line 16 are converged toward the focal point FP at a location where the center axis of the bypass line 16 crosses the laser light. Thus, most of the particles P flowing through the bypass line 16 are made to pass through the laser light, without the need of broadening the laser light into a belt-shape or without the inside of the bypass line 16 being scanned by the laser light, making it possible to accurately detect the number of or the size of particles P flowing through the bypass line 16. Since N₂ gas or the like passes through the gap 25 formed at the outer periphery of the particle converging member 23, the conductance of gas flow can be prevented from being lowered, thereby preventing a reduction in the efficiency of discharging N₂ gas or the like from the chamber 11.

In the above described apparatus 10, N₂ gas or the like is introduced toward a location other than the focal point FP, and therefore, the flow of N₂ gas or the like does not disturb the flow of particles P at or near the focal point FP, thus making it possible to more accurately detect the number of or the size of particles P flowing through the bypass line 16.

In the above described apparatus 10, upon detection of the number or size of the particles P, the pressure in the bypass line 16 in the vicinity of the ISPM 20 is set to a value falling within a range from 100 Pa to 10 kPa. When the pressure falls within a range from 100 Pa to 10 kPa, an inertia force acting on the particles P is relatively large, and therefore, the flow of the particles P is hardly disturbed by the flow of N₂ gas or the like. Thus, it is possible to efficiently converge the particles toward the focal point FP.

In the above described apparatus 10, the particle converging member 23 is formed with the through hole 24 facing the focal point FP, and the gap 25 is formed at the outer periphery of the converging member 23. Thus, by causing the particles P to pass through the through hole 24, the particles P can efficiently be converged toward the focal point FP, and it is ensured that a flow of N₂ gas or the like is prevented from being generated that disturbs a flow of particles P at or near the focal point FB.

In the above described apparatus 10, it is preferable that the particle converging member 23 should have a smooth surface so that particles P colliding with the converging member 23 are not caught by the member 23.

Next, an explanation will be given of a substrate processing apparatus, especially, a particle monitor system thereof, according to a second embodiment of this invention.

This embodiment is basically the same in construction and function as the first embodiment and only differs in the construction of a particle converging unit. In the following, only different construction and function will be described, with explanations of the same or similar construction and function omitted.

In this embodiment, to converge particles flowing through the bypass line 16, there is disposed a particle converging unit 26, which will be described below.

Figure 3:
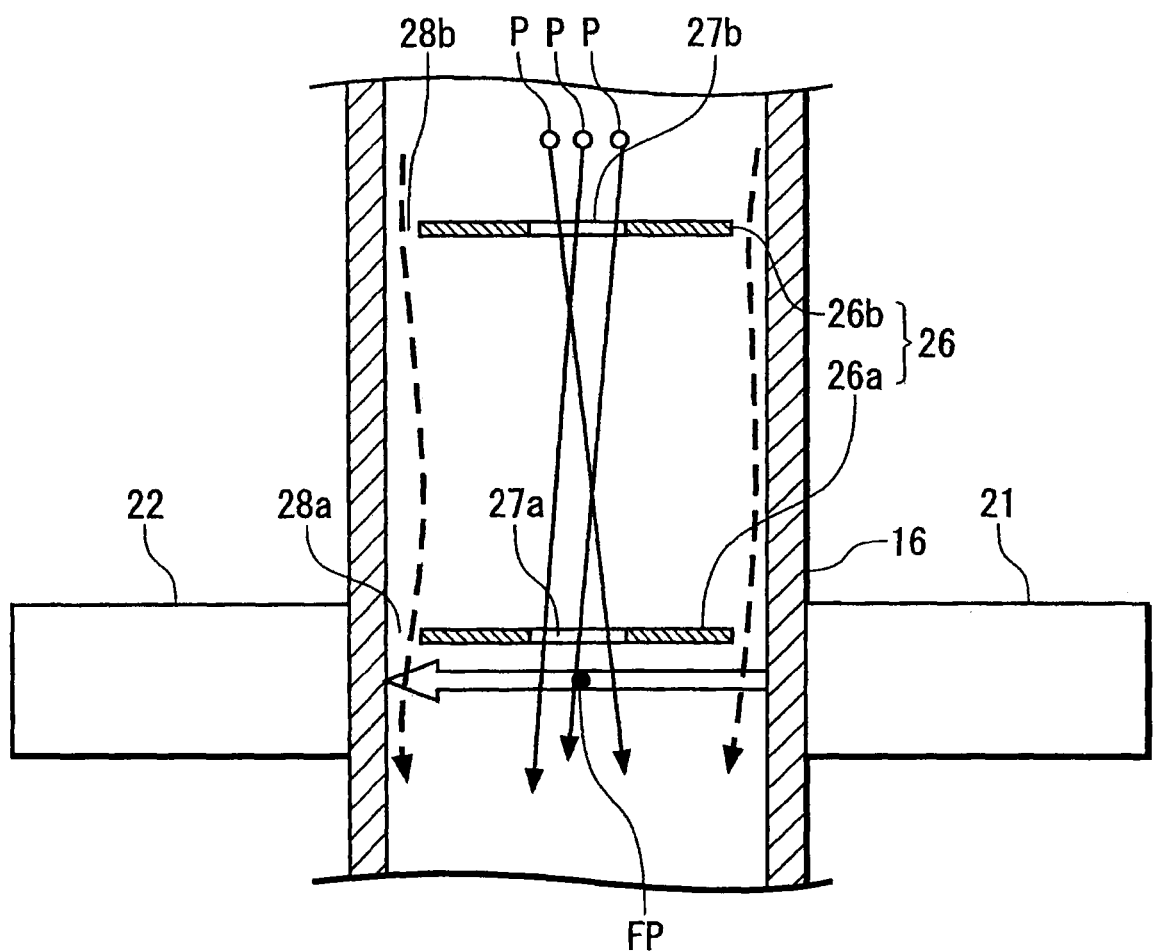
FIG. 3 is a section view showing a particle converging unit according to a second embodiment of this invention in a state disposed in a bypass line.

FIG. 3 shows in section view the particle converging unit 26 in a state disposed in the bypass line 16. In FIG. 3, laser light is indicated by white blank arrow.

As shown in FIG. 3, the particle converging unit 26 is comprised of two circular disk-like members 26a, 26b disposed in tandem in the bypass line 16. The disk-like members 26a, 26b have central parts thereof formed with through holes 27a, 27b and outer diameters smaller than the inner diameter of the bypass line 16 by a predetermined value, e.g., 5 mm.

In the bypass line 16, the disk-like members 26a, 26b are respectively disposed on the downstream side and the upstream side. Specifically, the disk-like member 26a is disposed upstream of the focal point FP of the photo multiplier tube 22 by a predetermined value, e.g., 10 mm. In addition, the disk-like members 26a, 26b are disposed to coincide with the center axis of the bypass line 16. Thus, the through holes 27a, 27b face the focal point FP, and there are gaps 28a, 28b (gas passage) between the bypass line 16 and the outer peripheries of the disk-like members 26a, 26b.

The circular disk-like members 26a, 26b are disposed to obstruct the bypass line 16, and therefore, particles P flowing through the bypass line 16 first pass through the through hole 27b of the disk-like member 26b, and then pass through the through hole 27a of the disk-like member 26a. Since these two through holes 27a, 27b are located on the center axis of the bypass line 16, particles P moving approximately in parallel to the center axis in the vicinity of the center axis mainly pass through the through holes 27a, 27b. Thus, the particle converging unit 26 mainly permits those particles P which are moved nearly parallel to and in the vicinity of the center axis of the bypass line 16 to pass through the unit 26, whereby it is ensured that the particles P are converged toward the focal point FP.

As shown by dotted lines in FIG. 3, N₂ gas or the like flowing through the bypass line 16 passes through the gaps 28a, 28b from upstream toward downstream. Since the gaps 28a, 28b are formed at the outer periphery of the particle converging member 23, N₂ gas or the like is guided by these gaps to flow toward locations other than the focal point FP.

In this embodiment, the laser oscillator 21 cooperates with the photo multiplier tube 22 and the particle converging unit 26 to constitute the particle monitor system.

With the substrate processing apparatus 10 of this embodiment including the particle monitor system, the particle converging unit 26 is comprised of the two circular disk-like members 26a, 26b disposed in tandem and formed with the through holes 27a, 27b facing the focal point FP. By causing particles P to pass through the through holes 27a, 27b, therefore, it is ensured that the particles P are converged toward the focal point FP located at a location where the center axis of the bypass line 16 crosses the laser light.

Next, an explanation will be given of a substrate processing apparatus, especially, a particle monitor system thereof, according to a third embodiment of this invention.

This embodiment is basically the same in construction and function as the first embodiment and only differs in the construction of the particle converging unit. In the following, only different construction and function will be described, with explanations of the same or similar construction and function omitted.

In this embodiment, to converge particles flowing through the bypass line 16, there is disposed a particle converging unit 29, which will be described below.

Figure 4A:
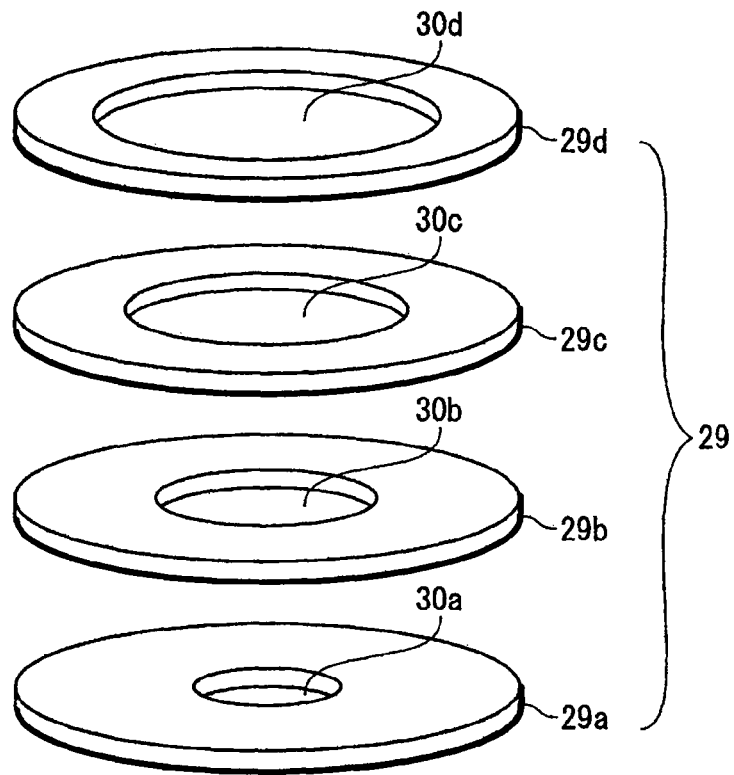
FIG. 4A is a perspective view schematically showing the construction of a particle converging unit according to a third embodiment of this invention.
Figure 4B:
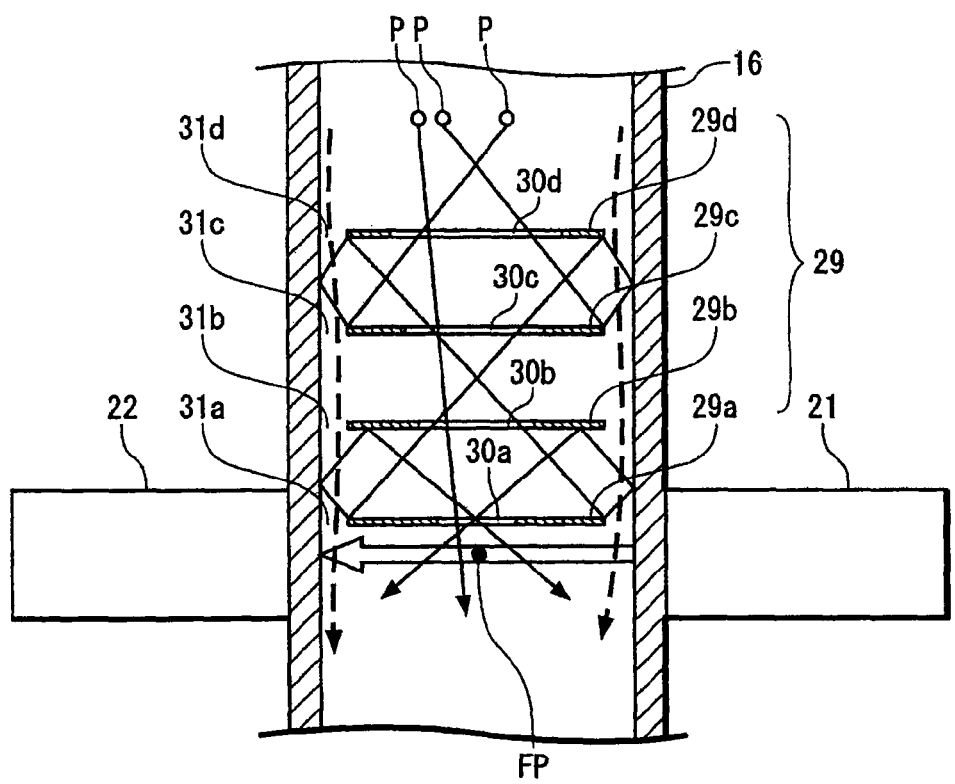
FIG. 4B is a section view showing the particle converging unit in a state arranged in a bypass line.

FIG. 4A schematically shows in perspective view the construction of the particle converging unit 29, and FIG. 4B shows in section view the unit 29 in a state arranged in the bypass line 16. In FIG. 4B, laser light is indicated by white blank arrow.

As shown in FIG. 4A, the particle converging unit 29 is comprised of four circular disk-like members 29a to 29d disposed in tandem in the bypass line 16. The disk-like members 29a to 29d have outer diameters smaller than the inner diameter of the bypass line 16 by a predetermined value, e.g., 5 mm, and have their central parts respectively formed with through holes 30a to 30d.

In the bypass line 16, the disk-like members 29a to 29d are disposed from the downstream side to the upstream side in this order. Specifically, the disk-like member 29a is disposed upstream of the focal point FP of the photo multiplier tube 22 by a predetermined value, e.g., 10 mm. Since the disk-like members 29a to 29d are disposed so that their centers coincide with the center axis of the bypass line 16, the through holes 30a to 30d face the focal point FP. Those of the through holes 30a to 30d which are disposed closer to the focal point FP are made smaller in diameter. Between the inner periphery of the bypass line 16 and the outer peripheries of the disk-like members 29a to 29d, gaps 31a to 31d (gas passage) are defined.

Since the disk-like members 29a to 29d are disposed to obstruct the bypass line 16, most of particles P flowing through the bypass line 16 pass through the through holes 30b to 30d while colliding with the disk-like members 29a to 29d, and finally pass through the through hole 30a formed in the disk-like member 29a. Since those of the through holes 30a to 30d which are located closer to the focal point FP are smaller in diameter, the flow of particles P passing through the through holes 30a to 30d is straightened toward the focal point FP. As a result, the particles P having passed through the through holes 30a to 30d naturally pass through the vicinity of the focal point FP. In other words, the particle converging unit 29 converges most of the particles P toward the focal point FP.

As shown by dotted lines in FIG. 4B, $N_2$ gas or the like flowing through the bypass line 16 is caused to pass through the gaps 31a to 31d from the upstream side to the downstream side. Since the gaps 31a to 31d are formed at the outer periphery of the particle converging unit 29, the $N_2$ gas or the like is guided by the gaps to flow toward locations other than the focal point FP.

In this embodiment, the laser oscillator 21 cooperates with the photo multiplier tube 22 and the particle converging unit 29 to constitute the particle monitor system.

With the substrate processing apparatus of this embodiment including the particle monitor system, those of the disk-like members 29a to 29d of the particle converging unit 29 which are disposed closer to the focal point FP are made smaller in diameter of the through holes 30a to 30d. By causing particles P to pass through the through holes 30a to 30d, therefore, a flow of the particles P can be straightened toward the focal point FP, making it possible to positively converge the particles P toward the focal point FP located at a location where the center axis of the bypass line 16 crosses the laser light.

Next, an explanation will be given of a substrate processing apparatus, especially, a particle monitor system thereof, according to a fourth embodiment of this invention.

This embodiment is basically the same in construction and function as the first embodiment and only differs in the construction of the particle converging unit. In the following, only different construction and function will be described, with explanations of the same or similar construction and function omitted.

In this embodiment, to converge particles flowing through the bypass line 16, a particle converging unit 32 is disposed, which will be described below.

Figure 5A:
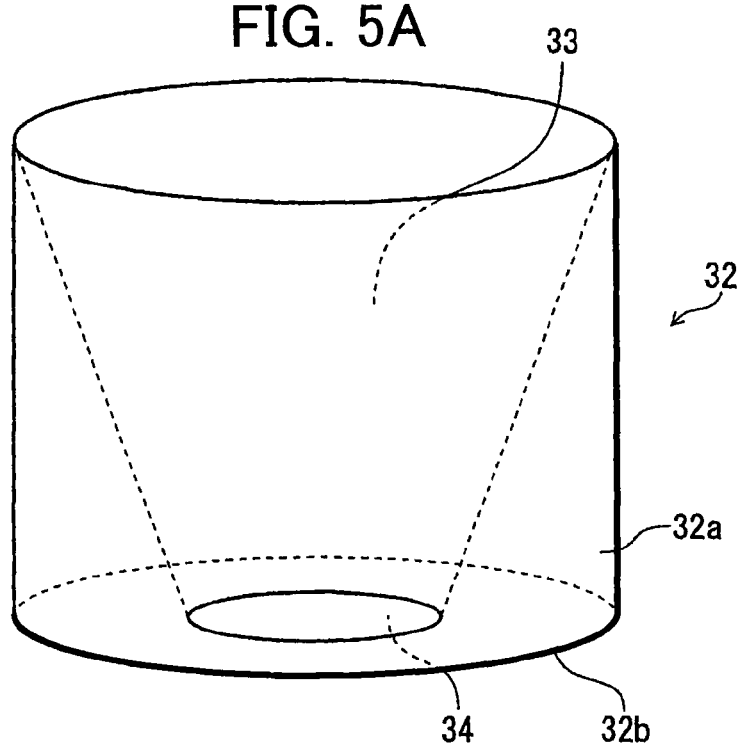
FIG. 5A is a perspective view schematically showing the construction of a particle converging unit according to a fourth embodiment of this invention.
Figure 5B:
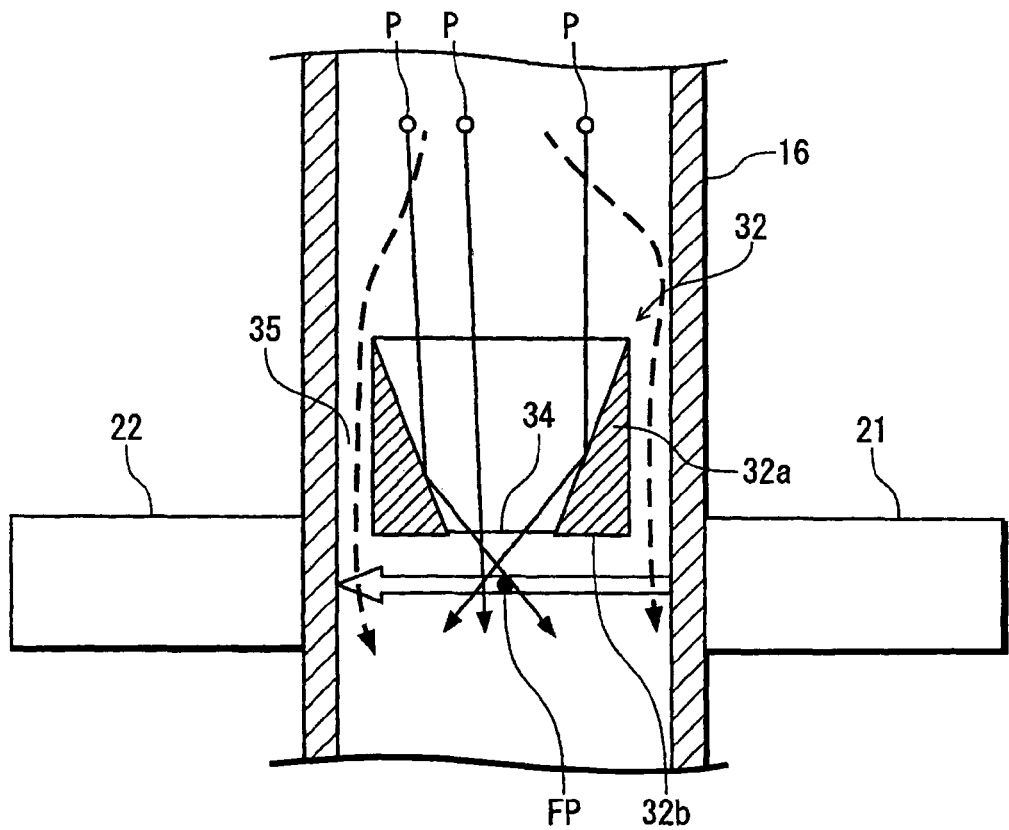
FIG. 5B is a section view showing the particle converging unit in a state arranged in a bypass line.

FIG. 5A schematically shows in perspective view the construction of the particle converging unit 32, and FIG. 5B shows in section view the particle converging unit 32 in a state arranged in the bypass line 16. In FIG. 5B, laser light is indicated by white blank arrow.

As shown in FIG. 5A, the particle converging unit 32 is comprised of a funnel-shaped member 32a including a cylindrical member formed with a mortar-shaped concave portion 33. The concave portion 33 has a bottom portion thereof formed with an opening 34 that opens to a bottom surface 32b of the funnel-shaped member 32a. The concave portion 33 is communicated via the opening 34 with a space facing the bottom surface 32b of the funnel-shaped member 32a whose outer diameter is smaller than the inner diameter of the bypass line 16 by a predetermined value, e.g., 5 mm.

In the bypass line 16, the particle converging unit 32 is disposed such that the bottom surface 32b of the funnel-shaped member 32a is positioned at a location upstream of the focal point FP of the photo multiplier tube 22 by a predetermined value, e.g., 10 mm, and the center axis of the concave portion 33 coincides with that of the bypass line 16. The opening 34 faces the focal point FP. The diameter of the concave portion 33 becomes smaller toward the focal point FP. Between the bypass line 16 and the funnel-shaped member 32a, a gap 35 (gas passage) is defined.

Since the funnel-shaped member 32a is disposed to obstruct the bypass line 16, most of particles P flowing through the bypass line 16 enter the concave portion 33 and finally pass through the opening 34 after colliding with a circumferential surface of the concave portion 33 and the like. Since the diameter of the concave portion 33 becomes smaller toward the focal point FP, a flow of particles P entering the concave portion 33 is straightened toward the focal point FP. As a result, the particles P having passed through the opening 34 naturally pass through the vicinity of the focal point FP. In other words, the particle converging unit 32 converges most of the particles P toward the focal point FP.

As shown by dotted lines in FIG. 5B, $N_2$ gas or the like flowing through the bypass line 16 is caused to pass through the gap 35 from the upstream side to the downstream side. Since the gap 35 is formed at the outer periphery of the particle converging unit 32, the $N_2$ gas or the like is guided by the gap 35 to flow toward locations other than the focal point FP.

In this embodiment, the laser oscillator 21 cooperates with the photo multiplier tube 22 and the particle converging unit 32 to constitute the particle monitor system.

With the substrate processing apparatus of this embodiment, especially, with the particle monitor system thereof, the funnel-shaped member 32a of the particle converging unit 32 includes the mortar-shaped concave portion 33 and the opening 34 formed in the bottom part of the concave portion 33.

Since the diameter of the concave portion 33 becomes smaller toward the focal point FP and the opening 34 is disposed to face the focal point FP, it is possible to efficiently converge the particles P toward the focal point FP located at a location where the center axis of the bypass line 16 crosses the laser light, by causing the particles P to enter the concave portion 33 and pass through the opening 34. Since the gap 35 is formed at the outer periphery of the particle converging unit 32, $N_2$ gas or the like can be guided to flow toward locations other than the focal point FP, making it possible to positively prevent a gas flow that disturbs a flow of particles P at or near the focal point FP from being generated.

In the above described particle converging unit 32, one or more through holes extending from the concave portion 33 to the outer periphery of the funnel-shaped member 32a can be formed. In that case, $N_2$ gas or the like entering the concave portion 33 can be discharged via the through holes to the gap 35, whereby a reduction in conductance of gas flow can positively be prevented.

Next, an explanation will be given of a substrate processing apparatus, especially, a particle monitor system thereof, according to a fifth embodiment of this invention.

This embodiment is basically the same in construction and function as the first embodiment and only differs in the construction of the particle converging unit. In the following, only different construction and function will be described, with explanations of the same or similar construction and function omitted.

Figure 6A:
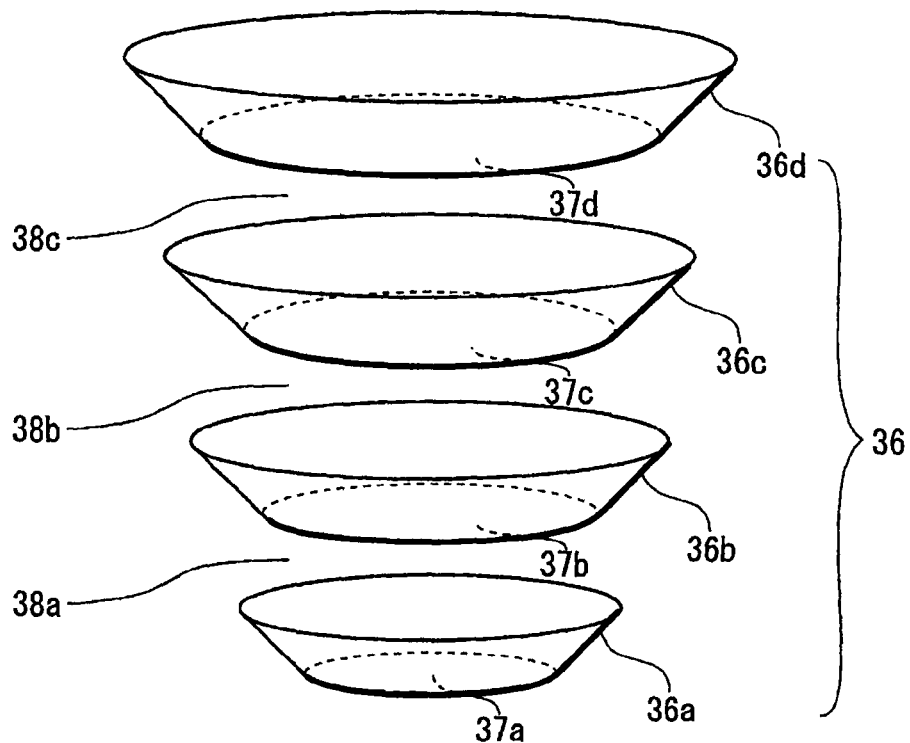
FIG. 6A is a perspective view schematically showing the construction of a particle converging unit according to a fifth embodiment of this invention.
Figure 6B:
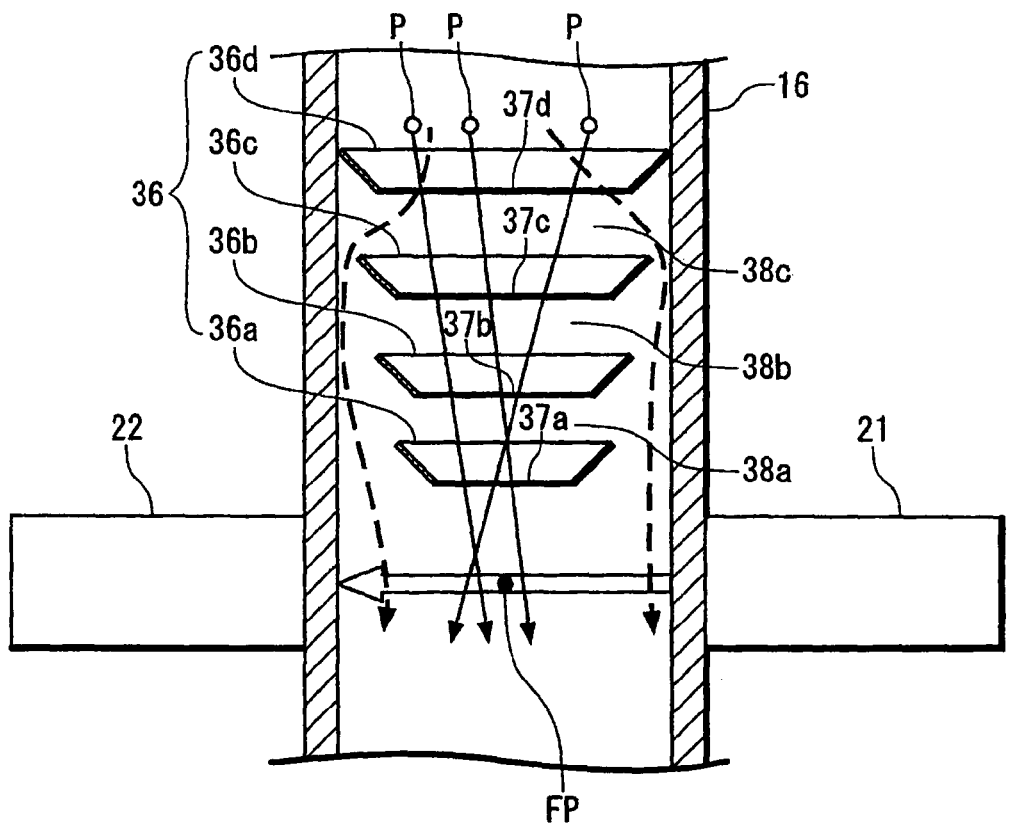
FIG. 6B is a section view showing the particle converging unit in a state arranged in a bypass line.

FIG. 6A schematically shows in perspective view the construction of the particle converging unit of this embodiment, and FIG. 6B shows in section view the particle converging unit in a state arranged in the bypass line. In FIG. 6B, laser light is indicated by white blank arrow.

As shown in FIG. 6A, the particle converging unit 36 is comprised of four funnel-shaped members 36a to 36d disposed in tandem in the bypass line 16. The funnel-shaped members 36a to 36d are formed at their bottom portions with openings 37a to 37d, respectively.

In the bypass line 16, the funnel-shaped members 36a to 36d are disposed in this order from downstream side to upstream side. Since the funnel-shaped members 36a to 36d are disposed such that their centers coincide with the center axis of the bypass line 16, the openings 37a to 37d face the focal point FP. Those of the openings 37a to 37d which are disposed closer to the focal point FP are made smaller in size. Between the funnel-shaped members 36a to 36d, gaps 38a to 38c (gas passage) are defined.

Since the funnel-shaped members 36a to 36d are disposed to obstruct the bypass line 16, most of particles P flowing through the bypass line 16 are made to pass through the openings 37b to 37d while repeatedly colliding with the funnel-shaped members 36a to 36d, and finally pass through the opening 37a of the funnel-shaped member 36a. Since those of the openings 37a to 37d which are closer to the focal point FP are made smaller in size, a flow of particles P passing through the openings 37a to 37d is straightened toward the focal point FP. As a result, the particles P having passed through the openings 37a to 37d naturally pass through the vicinity of the focal point FP. Thus, the particle converging unit 36 converges most of the particles P toward the focal point FP.

As shown by dotted lines in FIG. 6B, $N_2$ gas or the like flowing through the bypass line 16 is made to pass through the gaps 38a to 38 from upstream side to downstream side.

In this embodiment, the laser oscillator 21 cooperates with the photo multiplier tube 22 and the particle converging unit 36 to constitute the particle monitor system.

With the substrate processing apparatus of this embodiment, especially, with the particle monitor system thereof, those of the funnel-shaped members 36a to 36d of the particle converging unit 36 which are disposed closer to the focal point FP are made smaller in the size of the openings 37a to 37d, and the flow of particles P can be straightened toward the focal point FP by causing the particles P to pass through the openings 37a to 37d. Thus, the particles P can positively be converged toward the focal point FP located at a location where the center axis of the bypass line 16 crosses the laser light.

Next, an explanation will be given of a substrate processing apparatus, especially, a particle monitor system thereof, according to a sixth embodiment of this invention.

This embodiment is basically the same in construction and function as the first embodiment and only differs in the construction of the particle converging unit. In the following, only different construction and function will be described, with explanations of the same or similar construction and function omitted.

In this embodiment, to converge particles flowing through the bypass line 16, a particle converging unit 39 is disposed, which will described below.

Figure 7A:
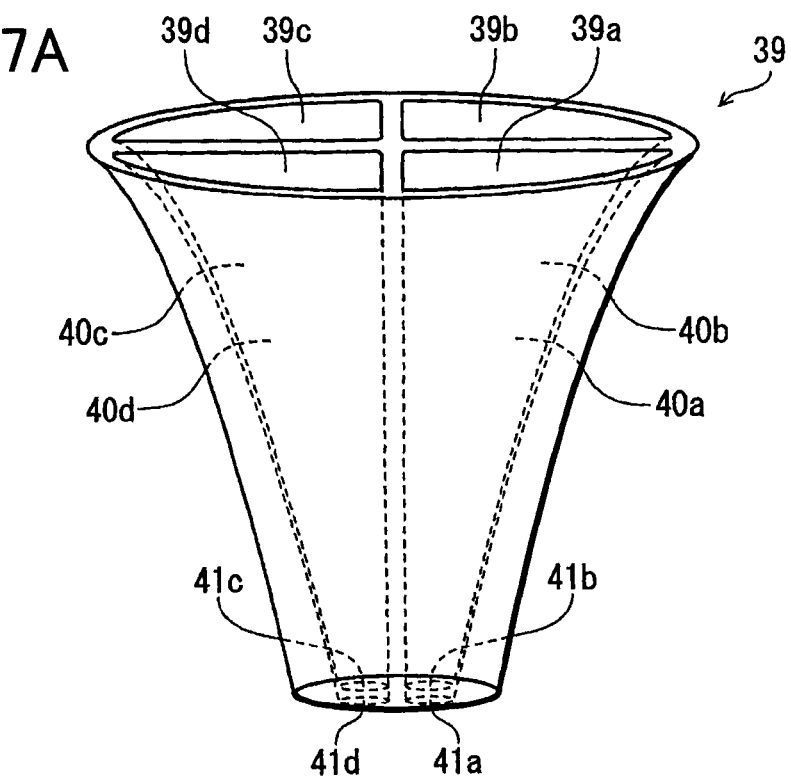
FIG. 7A is a perspective view schematically showing the construction of a particle converging unit according to a sixth embodiment of this invention.
Figure 7B:
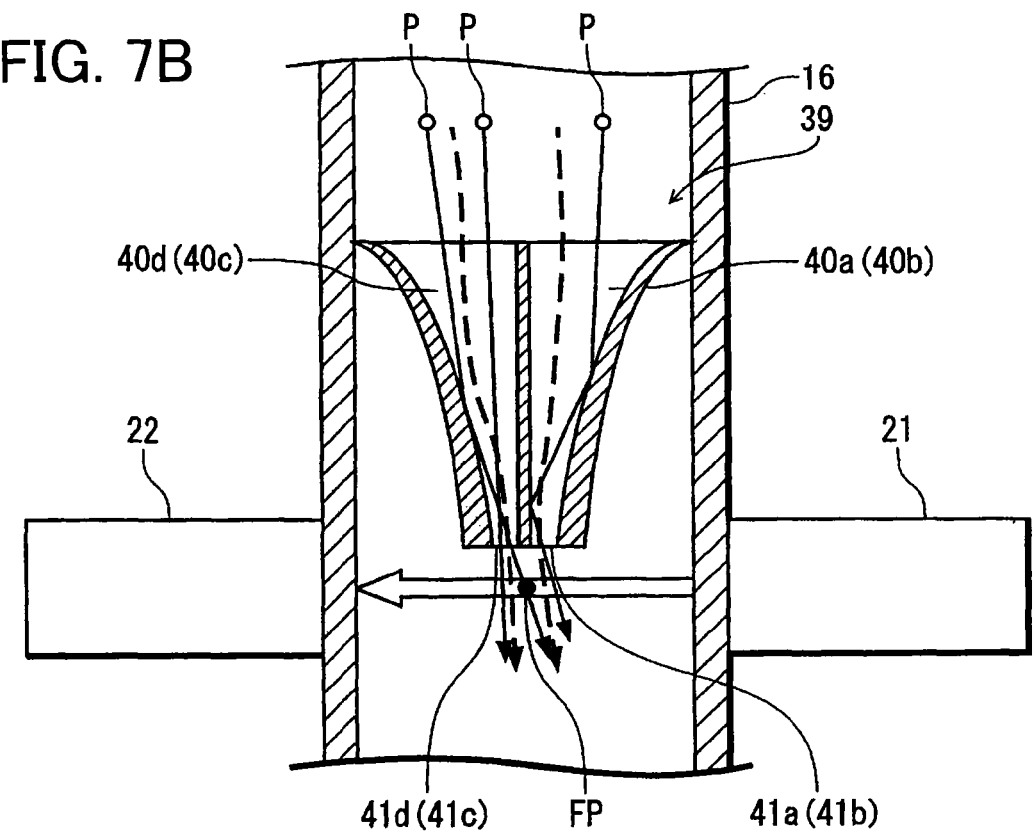
FIG. 7B is a section view showing the particle converging unit in a state arranged in a bypass line.

FIG. 7A schematically shows in perspective view the construction of the particle converging unit 39, and FIG. 7B shows in section view the unit 39 arranged in the bypass line 16. In FIG. 7B, laser light is indicated by white blank arrow.

As shown in FIG. 7A, the particle converging unit 39 is comprised of four tubular members 39a to 39d formed into one piece and each formed into a shape tapered toward downstream of the bypass line 16. Thus, passages 40a to 40d formed inside the tubular members are each formed into a tapered shape. The tubular members 39a to 39d have tip ends thereof formed with openings 41a to 41d, respectively, and the passages 40a to 40d are in communication via the openings 41a to 41d with a space facing the tip ends of the tubular members 39a to 39d.

In the bypass line 16, the particle converging unit 39 is disposed such that the lower end of the unit 39 is positioned at a location upstream of the focal point FP of the photo multiplier tube 22 by a predetermined value, e.g., 10 mm, and that the openings 41a to 41d face the focal point FP. The particle converging unit 39 has its upper end whose outer periphery is in contact with the inner surface of the bypass line 16 over the entire circumference thereof. In other words, the particle converging unit 39 is disposed to obstruct the bypass line 16. Therefore, most of the particles P flowing through the bypass line 16 enter the passages 40a to 40d, collide with peripheral surfaces of the passages 40a to 40d and the like, and finally pass through the openings 41a to 41d. Since the openings 41a to 41d are disposed to face the focal point FP, a flow of the particles P entering the passages 40a to 40d is straightened toward the focal point FP. As a result, the particles P having passed through the openings 41a to 41d naturally pass through the vicinity of the focal point FP. Thus, the particle converging unit 39 converges most of the particles P toward the focal point FP.

As shown by dotted lines in FIG. 7B, in the particle converging unit 39, $N_2$ gas or the like enters the passages 40a to 40d and finally passes through the openings 41a to 41d (gas passages).

In this embodiment, the laser oscillator 21 cooperates with the photo multiplier tube 22 and the particle converging unit 39 to form the particle monitor system.

With the substrate processing apparatus of this embodiment, especially, with the particle monitor system thereof, the four tubular members 39a to 39d of the particle converging unit 39 are each formed into a shape tapered toward the downstream side of the bypass line 16 and formed at their tip ends with openings 41a to 41d facing the focal point FP, and $N_2$ gas or the like is made to pass through the openings 41a to 41d. By causing particles P to pass through the openings 41a to 41d, therefore, the particles P can efficiently be converged toward the focal point FP located on the laser light and the $N_2$ gas or the like can be made to pass through a plurality of openings 41a to 41d, whereby the conductance of the gas flow can positively be prevented from being reduced.

Next, an explanation will be given of a substrate processing apparatus, especially, a particle monitor system thereof, according to a seventh embodiment of this invention.

This embodiment is basically the same in construction and function as the first embodiment and only different in that it comprises a vortex flow generator instead of the particle converging unit. In the following, only different construction and function will be described, with explanations of the same or similar construction and function omitted.

In this embodiment, to converge particles flowing through the bypass line 16, there is disposed a vortex generator 42, which will be described below.

Figure 8A:
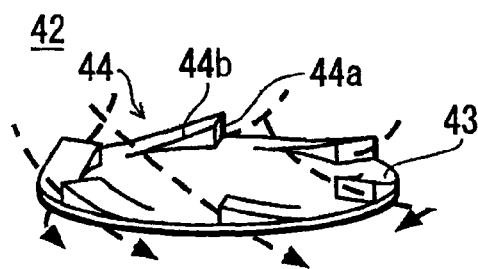
FIG. 8A is a perspective view schematically showing the construction of a vortex generator as a vortex flow generator according to a seventh embodiment of this invention.
Figure 8B:
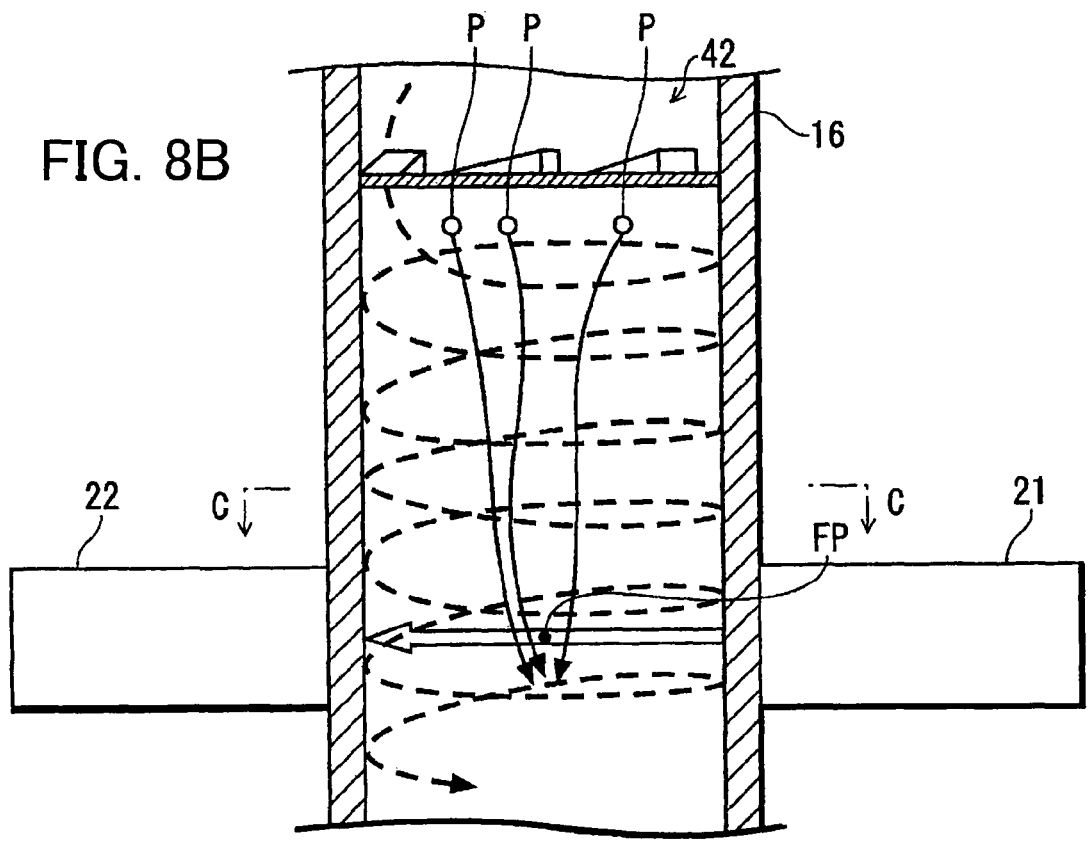
FIG. 8B is a section view showing a vortex flow generated in a bypass line.
Figure 8C:
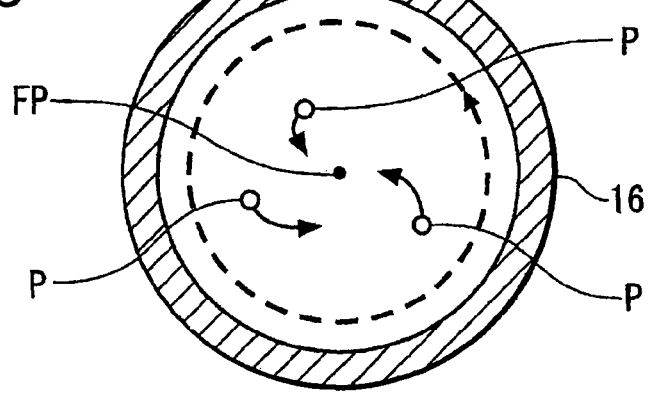
FIG. 8C is a section view taken along line C-C in FIG. 8B.

FIG. 8A schematically shows in perspective view the construction of the vortex generator 42 as a vortex flow generator, FIG. 8B shows in cross section a vortex flow generated in the bypass line 16, and FIG. 8C is a section view taken along line C-C in FIG. 8B. In FIG. 8B, laser light is indicated by white blank arrow.

As shown in FIG. 8A, the vortex generator 42 (vortex flow generator) includes a circular disk-shaped main body 43 and six gas introducing portions 44 disposed at equal intervals along an outer periphery of the main body 43. The main body 43 has a diameter equal to the inner diameter of the bypass line 16. Each of the gas introducing portions 44 includes an opening 44a formed in an upper surface of the main body 43, a through hole (not shown) formed to extend through the main body 43 at a location spaced from the opening 44a by a predetermined distance in the circumferential direction of the main body 43, and a hood 44b through which the opening 44a is communicated with the through hole. The hood 44b is formed circumferentially of the main body 43.

In the bypass line 16, the vortex generator 42 is disposed upstream of the focal point FP of the photo multiplier tube 22 to obstruct the bypass line 16. In this arrangement, $N_2$ gas or the like flowing through the bypass line 16 enters the gas introducing portions 44 via the openings 44a. The $N_2$ gas or the like entering the gas introducing portions 44 is guided by the hoods 44b into the through holes from which the $N_2$ gas or the like is injected. Since the hoods 44b are formed circumferentially of the main body 43, the $N_2$ gas or the like is injected from the through holes in the circumferential direction. In the bypass line 16, the $N_2$ gas or the like injected from the through holes generates a vortex flow that rotates around the center axis of the bypass line 16 (FIG. 8B). The generated vortex flow applies a centripetal force to particles P flowing through the bypass line 16, and the particles P are moved toward the center axis of the bypass line 16 (FIG. 8C). As a result, the particles P are converged toward the focal point FP located at a location where the center axis of the bypass line 16 crosses the laser light.

In this embodiment, upon detection of the number of or the size of particles P, the pressure in the bypass line 16 is set to a value falling within a rage from 1000 Pa (7.5 Torr) to 100 kPa (750 Torr). At a higher pressure, a viscous force of $N_2$ gas or the like becomes larger and more strongly acts on the particles P, and therefore, a centripetal force is made to be positively transmitted to the particles P.

In this embodiment, the laser oscillator 21 cooperates with the photo multiplier tube 22 and the vortex generator 42 to constitute the particle monitor system.

With the substrate processing apparatus of this embodiment, especially, with the particle monitor system, a vortex flow of $N_2$ gas or the like rotating around the center axis of the bypass line 16 is generated by the vortex generator 42. The vortex flow of $N_2$ gas or the like applies a centripetal force to particles P flowing through the bypass line 16, and therefore, the particles P are converged toward the focal point FP located at a location where the center axis of the bypass line 16 crosses laser light. Thus, without the need of broadening the laser light into a belt shape or without the inside of the bypass line 16 being scanned by the laser light, most of particles P flowing through the bypass line 16 can be made to pass through the laser light, whereby the number or size of particles flowing through the bypass line 16 can be detected with accuracy.

In this embodiment, upon detection of the number of or the size of particles P, the pressure in the bypass line 16 is set to a value falling within a range from 1000 Pa to 100 kPa. When the pressure falls within the range from 1000 Pa to 100 kPa, gas viscous force is improved and therefore a centripetal force can positively be applied to the particles, making it possible to ensure that the particles are converged toward the focal point FP.

The vortex flow generator used in the present invention is not limited to the above described vortex generator 42 but may be any other generator capable of generating a vortex flow rotating around the center axis of the bypass line 16.

Next, an explanation will be given of a substrate processing apparatus, especially, a particle monitor system thereof, according to an eighth embodiment of this invention.

This embodiment is basically the same in construction and function as the first embodiment and only different in that it comprises a cooling unit and the like instead of the particle converging unit. In the following, only different construction and function will be described, with explanations of the same or similar construction and function omitted.

In this embodiment, to converge particles flowing through the bypass line 16, a cooling unit 45 and a heater 46 are disposed, which will be described below.

Figure 9:
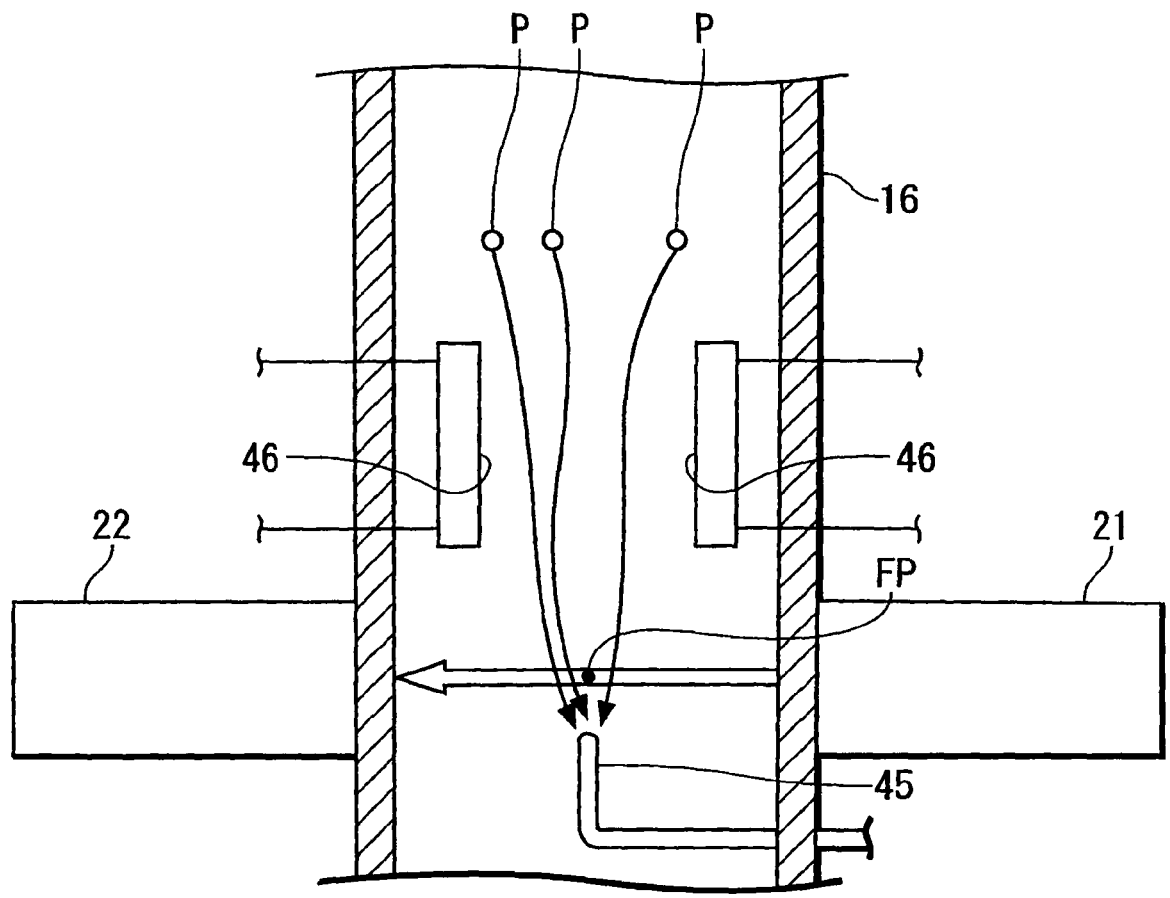
FIG. 9 is a section view showing a cooling unit and a heater according to an eighth embodiment of this invention in a state arranged in a bypass line.

FIG. 9 shows in cross section the cooling unit 45 and the heater 46 in a state arranged in the bypass line 16. In FIG. 9, laser light is indicated by white blank arrow.

As shown in FIG. 9, a thin rod-like cooling unit 45 is disposed downstream of the focal point FP in the bypass line 16, and two heaters 46 (heating unit) are disposed near the circumferential wall of the bypass line 16 at locations upstream of the focal point FP.

The cooling unit 45 has its tip end facing the focal point FP and adapted to be maintained at a low temperature by coolant flowing therethrough or by a peltiert device or the like incorporated therein. Thus, atmosphere around the focal point FP is cooled by the tip end of the cooling unit 45. The heaters 46 are each adapted to be kept at a high temperature by a heating wire or the like incorporated therein. Thus, atmosphere around the circumferential wall of the bypass line 16 are heated by the heaters 46. Since the focal point FP is positioned on the center axis of the bypass line 16, atmosphere other than atmosphere around the focal point FP is heated by the heaters 46.

When passing through the vicinity of the heaters 46, particles P flowing through the bypass line 16 receive heat from high temperature atmosphere near the heaters 46 and are moved by heat migrating force away from the vicinity of the heaters 46, i.e., away from high temperature atmosphere in the vicinity of the circumferential wall of the bypass line 16. On the other hand, atmosphere around the focal point FP is cooled, and thus the particles P do not receive heat from the atmosphere around the focal point FP. As a result, the particles P are converged toward the focal point FP.

In this embodiment, the laser oscillator 21 cooperates with the photo multiplier tube 22, the cooling unit 45, and the heater 46 to constitute the particle monitor system.

With the substrate processing apparatus of this embodiment, especially, with the particle monitor system thereof, atmosphere around the focal point FP is cooled and atmosphere around the circumferential wall of the bypass line 16 is heated. Particles P are moved away from high temperature atmosphere in the vicinity of the circumferential wall of the bypass line 16 by heat migrating force, and are hence converged toward the focal point FP located at a location at which the center axis of the bypass line 16 crosses the laser light. Thus, without the need of broadening the laser light into a belt-shape or the inside of the exhaust pipe 16 being scanned by the laser light, it is possible to cause most of particles flowing through the bypass line 16 to pass through the laser light, making it possible to accurately detect the number or the size of the particles flowing through the bypass line 16. In addition, since this embodiment does not require the provision of a plate-like member or the like for closing the bypass line 16, the conductance of gas flow can be prevented from being decreased.

Next, an explanation will be given of a substrate processing apparatus, especially, a particle monitor system thereof, according to a ninth embodiment of this invention.

This embodiment is basically the same in construction and function as the first embodiment and only differs in that it comprises a needle electrode and the like instead of the particle converging unit. In the following, only different construction and function will be described, with explanations of the same or similar construction and function omitted.

In this embodiment, to converge particles flowing through the bypass line 16, a needle electrode 47 and an electric charge generating unit 48 are disposed, which will be described below.

Figure 10:
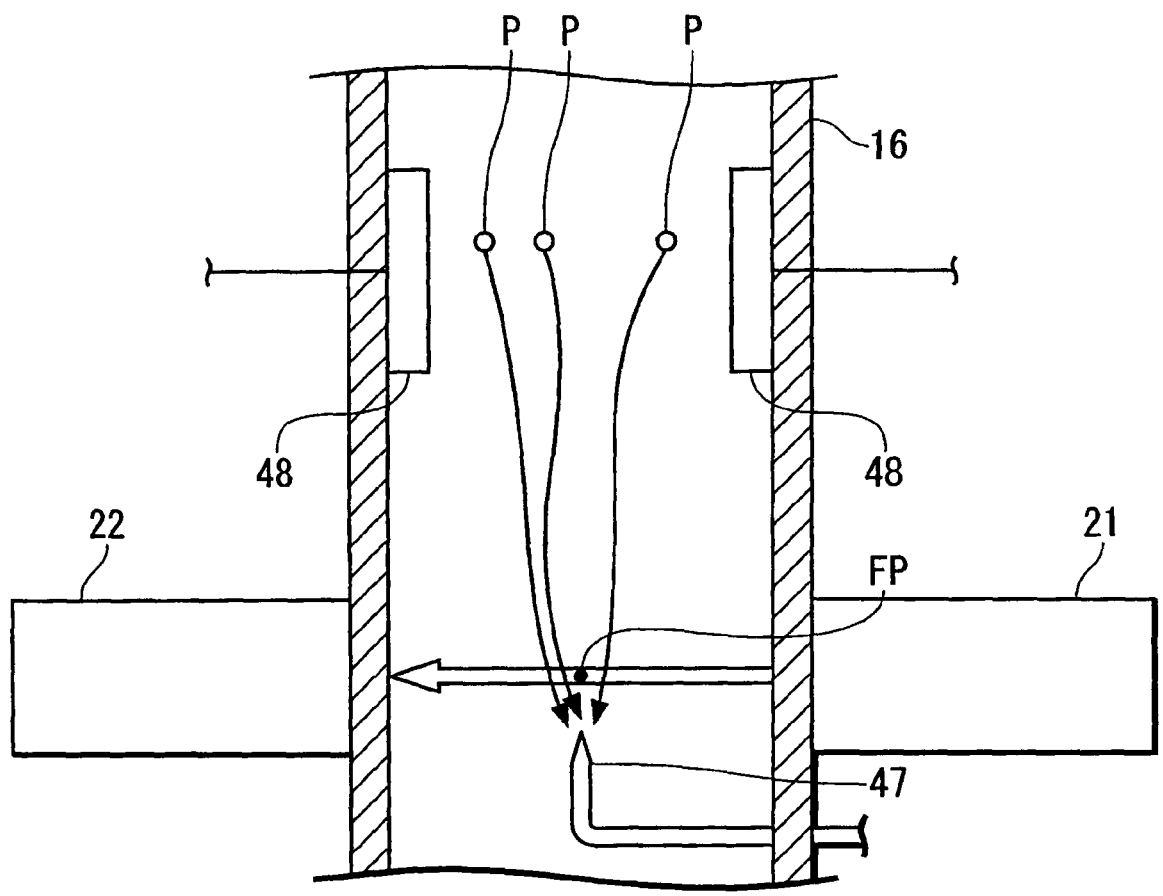
FIG. 10 is a section view showing a needle electrode and an electric charge generating unit according to a ninth embodiment of this invention in a state arranged in a bypass line.

FIG. 10 shows in cross section the needle electrode 47 and the electric charge generating unit 48 in a state disposed in the bypass line 16. In FIG. 10, laser light is indicated by white blank arrow.

As shown in FIG. 10, in the bypass line 16, the needle electrode 47 is disposed downstream of the focal point FP, and the electric charge generating unit 48 (charging device) is disposed on a side wall of the bypass line 16 at a location upstream of the focal point FP.

The needle electrode 47 has a tip end thereof facing the focal point FP and adapted to be applied with a predetermined voltage. The electric charge generating unit 48 is adapted to generate electric charge that traverses the inside of the bypass line 16. When passing through the generated electric charge, particles P are charged. An electrostatic force generated by the needle electrode 47 having a tip end thereof applied with a voltage acts on the charge particles P. Therefore, the particles P are attracted toward the tip end of the needle electrode 47 and thus attracted toward the vicinity of the focal point FP.

In this embodiment, the laser oscillator 21 cooperates with the photo multiplier tube 22, the needle electrode 47, and the electric charge generating unit 48 to constitute the particle monitor system.

The substrate processing apparatus of this embodiment, especially, the particle monitor system thereof, includes the charging device 48 disposed upstream of the focal point FP for causing particles P to be charged and the needle electrode 47 having a tip end thereof facing the focal point FP. Charged particles P charged by the charging device 48 are attracted toward the vicinity of the focal point FP by an electrostatic force generated by the needle electrode 47 having a tip end thereof applied with a voltage, whereby the particles P are converged toward the focal point FP located at a location where the center axis of the bypass line 16 crosses the laser light. Thus, without the need of broadening the laser light into a belt-shape or the inside of the bypass line 16 being scanned by the laser light, it is possible to cause most of the particles P flowing through the bypass line 16 to pass through the laser light, making it possible to accurately detect the number or the size of the particles P flowing through the bypass line 16. In addition, this embodiment does not require the provision of a plate-like member for closing the bypass line 16, the conductance of gas flow can be prevented from being decreased.

In the above described embodiments, semiconductor wafers W are used as substrates, but this is not limitative. For example, a glass substrate for use in such as LCD (Liquid Crystal Display) or FPD (Flat Panel Display) can be used as substrate.

What is claimed is:

1. A particle monitor system for detecting particles in a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising:

a laser oscillator adapted to irradiate laser light toward inside the exhaust pipe;

a light receiving device having a focal point thereof adapted to be located on the laser light, said light receiving device being adapted to receive scattered light or attenuated light of the laser light scattered or attenuated by particles flowing through the exhaust pipe; and a particle converging unit adapted to converge at least part of the particles toward the focal point of said light receiving device, wherein said particle converging unit includes a gas passage through which gas passes from upstream of the exhaust pipe to downstream thereof, and wherein the gas passage of said particle converging unit is adapted to separate a flow of the gas from a flow of the particles such that the gas is introduced toward a location other than the focal point of said light receiving device.

2. A particle monitor system for detecting particles in a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising:

a laser oscillator adapted to irradiate laser light toward inside the exhaust pipe;

a light receiving device having a focal point thereof adapted to be located on the laser light, said light receiving device being adapted to receive scattered light or attenuated light of the laser light scattered or attenuated by particles flowing through the exhaust pipe; and a particle converging unit adapted to converge at least part of the particles toward the focal point of said light receiving device, wherein said particle converging unit includes a gas passage through which gas passes from upstream of the exhaust pipe to downstream thereof, and wherein a pressure in the exhaust pipe upon detection of particles is set to a value in a range from 100 Pa to 10 kPa such that an inertia force acting on the particles become larger than a viscous force of the gas.

3. A particle monitor system for detecting particles in a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising:

a laser oscillator adapted to irradiate laser light toward inside the exhaust pipe;

a light receiving device having a focal point thereof adapted to be located on the laser light, said light receiving device being adapted to receive scattered light or attenuated light of the laser light scattered or attenuated by particles flowing through the exhaust pipe; and a particle converging unit adapted to converge at least part of the particles toward the focal point of said light receiving device, wherein said particle converging unit includes a gas passage through which gas passes from upstream of the exhaust pipe to downstream thereof, wherein said particle converging unit is comprised of at least one plate-like member disposed to obstruct the exhaust pipe, wherein the plate-like member is formed with a hole facing the focal point of said light receiving device, and wherein the gas passage of said particle converging unit is formed at a location other than a location where the hole of the plate-like member is formed.

4. The particle monitor system according to claim 3, wherein said particle converging unit is comprised of a plurality of the plate-like members, and holes formed in those of the plate-like members which are disposed closer to the focal point of said light receiving device are made smaller in diameter.

5. A particle monitor system for detecting particles in a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising:

a laser oscillator adapted to irradiate laser light toward inside the exhaust pipe;

a light receiving device having a focal point thereof adapted to be located on the laser light, said light receiving device being adapted to receive scattered light or attenuated light of the laser light scattered or attenuated by particles flowing through the exhaust pipe; and a particle converging unit adapted to converge at least part of the particles toward the focal point of said light receiving device, wherein said particle converging unit includes a gas passage through which gas passes from upstream of the exhaust pipe to downstream thereof, wherein said particle converging unit is comprised of at least one funnel-shaped member having a bottom portion thereof formed with an opening that faces the focal point of said light receiving device, and wherein the gas passage of said particle converging unit is formed at a location other than a location where the opening of the funnel-shaped member is formed.

6. The particle monitor system according to claim 5, wherein said particle converging unit is comprised of a plurality of the funnel-shaped members, and those of the funnel-shaped members which are disposed closer to the focal point of said light receiving device are made smaller in size of openings thereof.

7. A particle monitor system for detecting particles in a substrate processing apparatus including a housing chamber in which a substrate is received and processed, an exhausting apparatus for exhausting gas in the housing chamber therefrom to reduce a pressure in the housing chamber, and an exhaust pipe through which the housing chamber is communicated with the exhausting apparatus, comprising:

a laser oscillator adapted to irradiate laser light toward inside the exhaust pipe;

a light receiving device having a focal point thereof adapted to be located on the laser light, said light receiving device being adapted to receive scattered light or attenuated light of the laser light scattered or attenuated by particles flowing through the exhaust pipe; and a particle converging unit adapted to converge at least part of the particles toward the focal point of said light receiving device, wherein said particle converging unit includes a gas passage through which gas passes from upstream of the exhaust pipe to downstream thereof, wherein said particle converging unit is comprised of a plurality of tubular members each having a shape tapered toward downstream of the exhaust pipe and each having at its tip end an opening thereof facing the focal point of said light receiving device, and wherein each of the openings of said particle converging unit also serving as the gas passage of said particle converging unit.

* * * * *